United States Patent [19]

Kikuchi

[11] Patent Number: 4,947,246
[45] Date of Patent: Aug. 7, 1990

[54] COLOR ENDOSCOPE APPARATUS INCLUDING COLOR LIGHTING CONTROL

[75] Inventor: Katsuya Kikuchi, Tochiga, Japan

[73] Assignee: Kabushiki Kaisha Toshiba, Kawasaki, Japan

[21] Appl. No.: 369,934

[22] Filed: Jun. 22, 1989

[30] Foreign Application Priority Data

Jun. 29, 1988 [JP] Japan .................................. 63-159514

[51] Int. Cl.⁵ ........................... A61B 1/06; H04N 7/18
[52] U.S. Cl. ............................................. 358/98; 128/6
[58] Field of Search ..................... 358/98, 42, 12, 27, 358/28, 29, 213.14, 213.16; 128/4, 6

[56] References Cited

U.S. PATENT DOCUMENTS 4,653,478  3/1987  Nagasaki et al. ................. 358/98 X
4,800,424  1/1989  Noguchi ............................. 358/98

Primary Examiner—Howard W. Britton
Assistant Examiner—Victor R. Kostak
Attorney, Agent, or Firm—Foley & Lardner, Schwartz, Jeffery, Schwaab, Mack, Blumenthal & Evans

[57] ABSTRACT

In a frame sequentially scanning type color endoscope apparatus, a light chopper is employed in conjunction with a xenon lamp. The light chopper is constructed of a disk, three slots formed in a peripheral portion of the disk, and three different color filters mounted on the corresponding slots. Positions of two slots are juxtaposed with each other with respect to another position of the remaining slot. Three different color light pulses are produced from three color filters with having the substantially same duration times and different time intervals.

8 Claims, 5 Drawing Sheets

SYNC SIGNAL

PULSED LIGHT

SYNC SIGNAL

PULSED
LIGHT

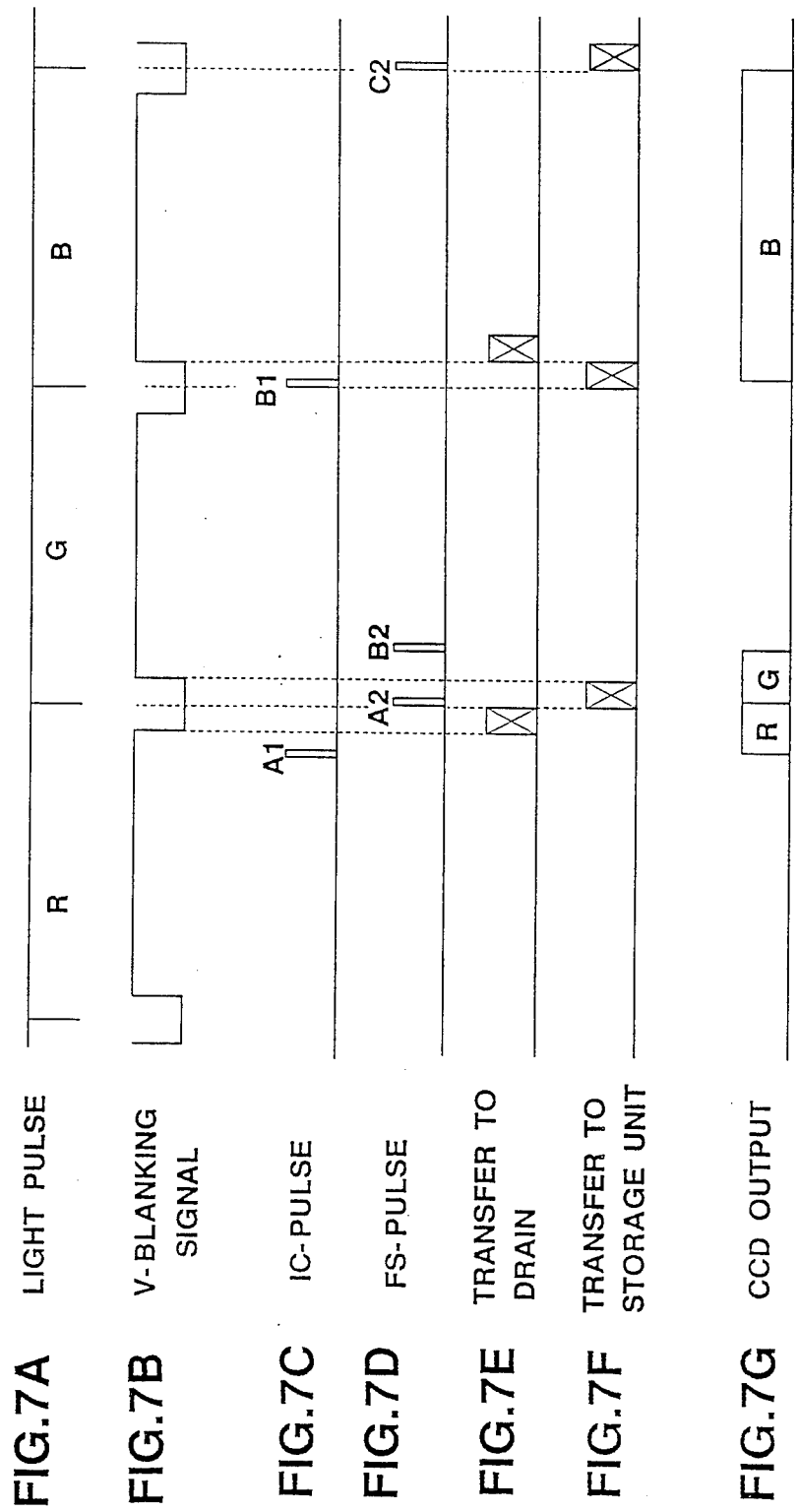

COLOR ENDOSCOPE APPARATUS INCLUDING COLOR LIGHTING CONTROL

BACKGROUND OF THE INVENTION

1. Field of the Invention

The present invention generally relates to a frame sequential scanning type color endoscope apparatus where three primary color light pulses, i.e., red, green and blue light pulses are sequentially projected toward an object under medical inspection so as to obtain a color image of the illuminated object. More specifically, the present invention is directed to a color lighting control of a light source unit employed in the frame sequential scanning type color endoscope apparatus.

2. Description of the Related Art

As is well known, in the above-described color endoscope apparatus, the three primary color light pulses, i.e., red, green and blue light pulses are sequentially projected toward the object under examination such as a stomach so as to acquire three color image signals, and thereafter, three color image signals are combined with each other, thereby obtaining one complete color image of the illuminated object, as a color endoscope image.

The above-identified color endoscope apparatus is described in, for instance, U.S. Pat. No. 4,621,281 issued on Nov. 4, 1986.

In the conventional color endoscope apparatus, there is a drawback that the correctly colored image of the illuminated object under examination cannot be reconstructed in case of rapid changes in the movement of the object illuminated by the three primary color light pulses. In other words, a mismatching may occur in the respective R, G, B-colored images due to the positional shifts when the rapidly changing object such as a stomach is illuminated by the three primary color lights. As a consequence, no correct color synthesization is performed in the resultant color image of the rapidly changing object. That is to say, a color misregistration may occur in the RGB color image of the rapidly changing object.

In addition to the above-described drawback, there is another problem in the conventional color endoscope apparatus. When the time durations of the R, G, B color light pulses are selected to be relatively long and the object under examination illuminated by these light pulses is rapidly moved during the light pulse illumination, blurs may be produced in the resultant color image. As a result, a resolution of the resultant color image may be deteriorated.

The present invention has been made in an attempt to solve the above-described drawbacks of the conventional color endoscope apparatus, and therefore has an object to provide a frame sequential scanning type color endoscope apparatus in which occurrences of the color misregistration in the RGB color images can be sufficiently suppressed, and also the blur phenomenon of the RGB color images caused by the rapidly changing object can be mitigated.

SUMMARY OF THE INVENTION

The present invention has been made in an attempt to solve the above-described problems, and therefore an object to provide a color endoscope apparatus comprises:

light source means (6) for sequentially producing three different color light pulses (R, G, B) in synchronism with a frame sequentially scanning operation, at least one of the color light pulses having a narrow duration time than other duration times of the remaining color light pulses and one time interval between two color light pulses being selected to be shorter than another time interval between the remaining color light pulse and one of said two color light pulses;

light conducting means (7) for sequentially receiving the three different color light pulses from the light source means (6) and for successively projecting the received three color light pulses toward an object under medical examination;

image signal producing means (9) for sequentially receiving light reflected from the illuminated object under medical examination so as to successively produce three different colored image signals of the illuminated object; and, image signal processing means (11 and 14-16) for processing the three different colored image signals derived from the image signal producing means (9) so as to obtain one complete color endoscope signal of the illuminated object.

BRIEF DESCRIPTION OF THE DRAWINGS

The invention is best understood to read the following specification in conjunction with the accompany drawings, in which.

DETAILED DESCRIPTION OF THE PREFERRED EMBODIMENTS

Recognitions

For a better understanding of the particular advantages achieved by the frame sequential scanning type color endoscope apparatus according to the invention, the Applicant conducted various experiments on the endoscope images and thus, can conclude the following recognitions.

First, a selection was made in the clinical images of the organs having rapid movements, for instance, stomach, esophagus, and duodenum. Then, an inspection was carried as to how each pixel of the clinical image data had been positionally shifted from an original pixel thereof within the frame period of the video endoscope image signal, i.e., 33 milliseconds. The results of this inspection were as follows:

Stomach and Duodenum .... approximately 2 to 3-pixel positional shifts.

Esophagus .............. approximately 10-pixel positional shifts.

Taking account of the above-described experimental results, it is concluded that when a time duration of one color light pulse is selected to be approximately 3 milliseconds, no blur phenomenon caused by the organ's movements may appear in the resultant endoscope image in case of the 10-pixel positional shifts.

Overall Arrangement of Endoscope Apparatus

Figure 1:
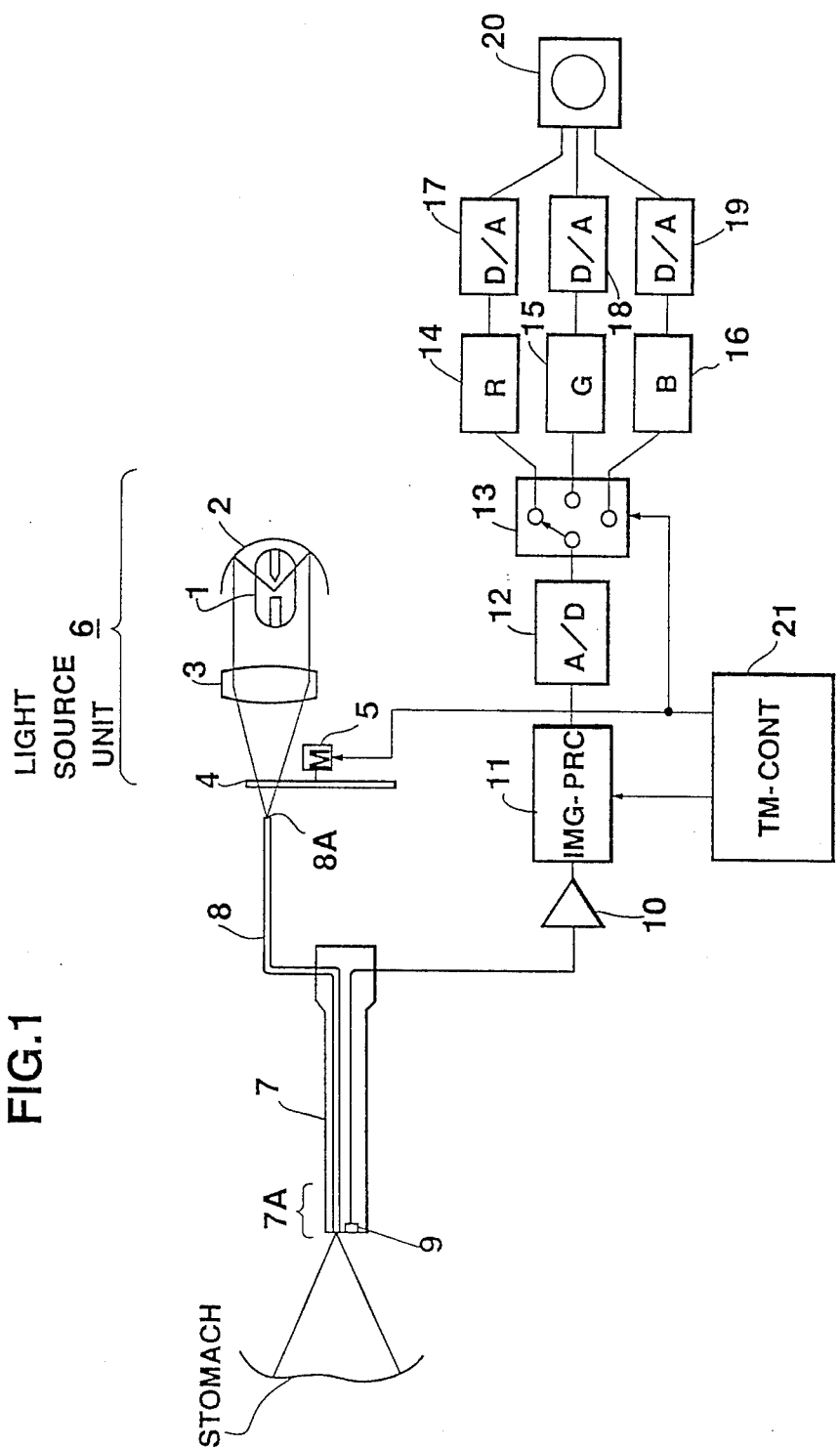
FIG. 1 is a schematic block diagram of a color endoscope apparatus according to a first preferred embodiment of the invention.

In FIG. 1, there is shown an overall arrangement of a frame sequentially scanning type color endoscope apparatus according to a first preferred embodiment of the invention.

The color endoscope apparatus according to the first preferred embodiment includes a light source unit 6 in which there are arranged a xenon lamp 1, a reflecting mirror 2, an optical lens 3 and a light chopper 4 driven by a motor 5. A light guide 8 is provided from the light source unit 6 to a tip portion 7A of an endoscope scope 7 in order to conduct the R(red), G(green) and B(blue) light pulses emitted from the light source unit 6 to the tip portion 7A of the scope 7.

A solid-state imaging element (for instance, a charge-coupled device) 9 is positioned at this tip portion 7A of the endoscope scope 7. A photo-conductive conversion output derived from CCD 9 is transmitted therefrom to an amplifier 10 provided at the endoscope apparatus' housing.

The amplifier 10 is further connected to a CCD image signal processing circuit 11, an analog-to digital (A/D) converter 12, a switching circuit 13, RGB image memories 14 to 16, RGB digital-to analog (D/A) converters 17 to 19, a color monitor 20, and a timing controller 21, as represented in FIG. 1.

The timing controller 21 transmit synchronization (sync) signals to the motor 5, CCD image signal processing circuit 11 and switching circuit 13 so as to perform the frame sequential scanning operation.

Construction of Light Chopper

Figure 2:
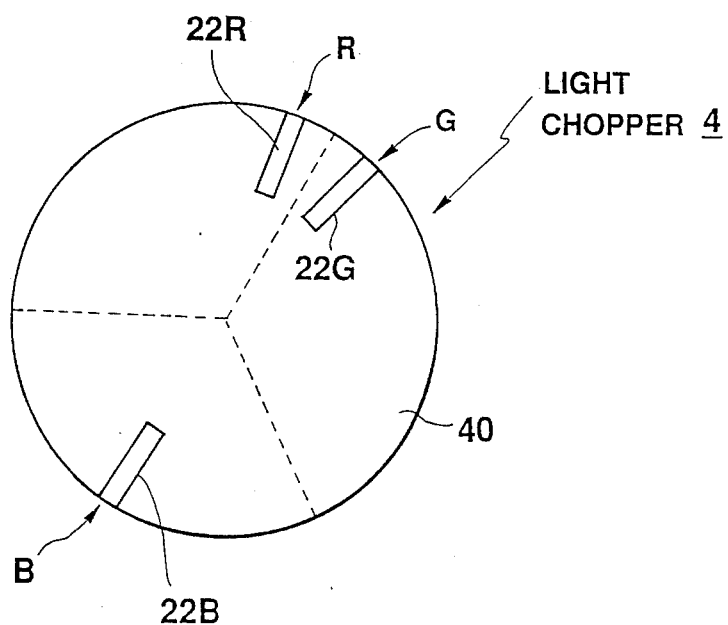
FIG. 2 schematically illustrates a light chopper 4 employed in the color endoscope apparatus shown in FIG. 1.

As previously described, the constructions of the light source unit 6 constitutes a major feature of the present invention. The light chopper 4 is so designed, as shown in FIG. 2, that three narrow slots, or channels 22R, 22G and 22B are formed in a peripheral portion of a disk 40 under the condition that the positions of two slots 22R and 22G are closely juxtaposed with each other, as compared with the remaining slot 22B. Furthermore, three different color filters R, G, and B are assembled within the corresponding three narrow slots 22R, 22G and 22B, through which three different color light pulses "R", "G", and "B" are penetrated. As is shown in FIG. 2, each of three slots 22R, 22G, and 22B is formed in the corresponding three-divided regions (denoted by a dot line) of the disk 40 along the circular direction.

With the above described constructions, while the light chopper 4 is rotated at a constant rotation speed by energizing the motor 5 under the control of the timing controller 21, three primary color light pulses R, G, and B are projected from the light source unit 6 to the endoscope scope 7 in synchronism with the frame sequential scanning operation.

Figure 3A:
FIG. 3A and 3B are a sync signal and RGB color light pulses produced from the light chopper 4 shown in FIG. 2.
Figure 3B:
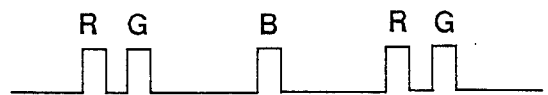

These three color light pulses are represented in a timing chart shown in FIG. 3B. The respective color light pulses R, G, B are emitted in synchronism with the sync signal as shown in FIG. 3A. In the first preferred embodiment, a time interval between the light pulses R and G is selected to be shorter than another time interval between the light pulse B and each of these light pulses R and B. As a result, neither the color misregistration in the resultant color image, nor the blur phenomenon appearing therein may occur according to the color endoscope apparatus according to the first preferred embodiment shown in FIGS. 1 to 3 (will be discussed later).

Overall Operation

Referring now to FIGS. 1 to 3, an overall operation of the frame sequential scanning type color endoscope apparatus according to the first preferred embodiment will be described. The light emitted from the xenon lamp 1 is transmitted via the reflecting mirror 2 and optical lens 3 and converged into a light inlet 8A of the light guide 8. While the light chopper 4 positioned between the optical lens 3 and the light inlet 8A of the light guide 8 is rotated at a constant speed by driving the motor 5, the above-described three different color light pulses R, G, and B are produced from the light chopper 4 in a predetermined pulse sequence as defined in FIG. 3B in synchronism with the frame sequential scanning operation.

Then, these color light pulses R, G, and B are sequentially conducted via the light guide 8 to the tip portion 7A of the scope 7, and thereafter projected to the object under examination, for instance, an inside wall of a stomach.

The light reflected from the inside wall of the stomach is photo-electrically converted into a CCD image signal by CCD 9. The CCD image signal derived from CCD 9 is transferred to the amplifier 10. The CCD image signal is amplified in the amplifier 10 to a predetermined signal level required for further signal processing operations. The amplified CCD image signal is processed by the CCD image signal processing circuit 11 in the known signal processes such as white balances and gamma corrections.

Thus, the CCD image signal processed in the signal processing circuit 11 is converted into the corresponding digital signal by the A/D converter 12. The R, C, and B digital signals constituting signal components of the A/D-converted CCD image signal are properly selected by the switching circuit 13 so as to be stored into the corresponding color image memories 14 to 16, respectively.

The three different color image data R, G, B which have been stored into the corresponding image memories 14 to 16 are simultaneously read out and thereafter converted into corresponding analog signals by the D/A converters 17 to 19, respectively. Then, the D/A-converted image signals are sent to the color monitor 20 where endoscope images of the illuminated stomach are displayed in the color mode.

In the above-described color endoscope operations, the following features of the color endoscope apparatus are achieved according to the first preferred embodiment. That is, since the light chopper 4 is so designed as shown in FIG. 2, the duration times of the respective color light pulses R, G, and B are shorter than those of the conventional color light pulses. As a result, even when the internal wall of the stomach under examination is rapidly moved during the endoscope examination, the blur phenomenon appearing in the endoscope image displayed on the color monitor 20 can be prevented.

In addition to the above-described first feature, one time interval between the two color light pulses "R" and "G" is considerably shorter than another time interval between the remaining color light pulse "B" and the color light pulse "R", or "G" as represented in FIG. 3B. As a consequence, the mismatching between the three different RGB color images due to the positional shifts can be prevented and therefore the color misregistration occurring in the RGB color images can be suppressed.

As a result of a detailed analysis in the color endoscope image, the following fact is found. That is to say, the resolution of the color endoscope image is mostly affected by the G-colored image. Also, the signal strength (amplitude) of the R-colored image signal is the highest, whereas that of the B-colored image signal is the lowest. In view of this inherent color image's feature, no specific care is required in the position of the B-colored filter, for instance, in the light chopper 4. )

Second Light Chopper

Figure 4:
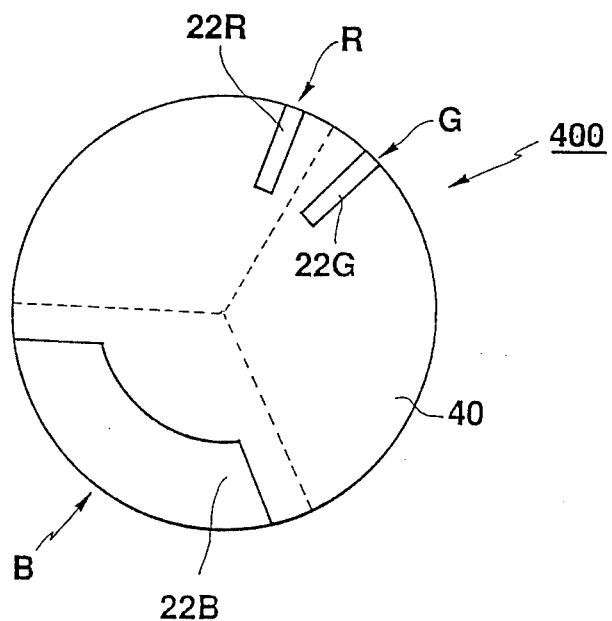
FIG. 4 schematically illustrates a light chopper 400 employed in a color endoscope apparatus according to a second preferred embodiment.

Referring now to FIGS. 4 and 5, a construction of a light chopper 400 and three primary color light pulses R, G, B derived therefrom according to a second preferred embodiment will be described.

As shown in FIG. 4, two slots having narrow widths 22R and 22G and one slot 23B having a wide width are formed in the peripheral portion of the disk 40 in such a manner that the positions of two slots having the narrow widths 22R and 22G are closely juxtaposed with each other.

Figure 5A:
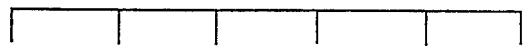
FIG. 5A and 5B are a sync signal and RGB color light pulses produced from the light chopper 400 shown in FIG. 4.
Figure 5B:
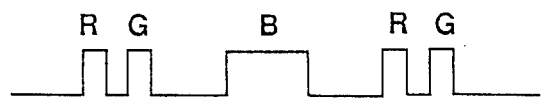

According to the second preferred embodiment, three different color light pulses R, G, and B are emitted from the light chopper 400 in relation to the sync signal as represented in FIGS. 5A and 5B. Since the light amount of the B-colored light component having low sensitivities becomes large, the signal-to-noise ratio of the resultant endoscope image can be improved.

In other words, the time interval between the light pulses "R" and "G" is shorter than another time interval between the remaining light pulse "B" and the other light pulse "R" or "G". Moreover, the duration time of the light pulse "B" is selected to be longer than those of the remaining light pulses "R" and "G", according to the feature of the second preferred embodiment of the invention.

Other Light Pulse Production

In accordance with the present invention, the three different color light pulses R, G, B may be produced by other way than the utilization of the above-described first and second light choppers 4 and 400, for instance, a control of a signal storage time period of a CCD (charge-coupled device).

The color light pulse production by way of controlling a signal storage time period of a CCD, according to a third preferred embodiment of the invention, will now be described with reference to FIGS. 6 and 7.

As a CCD whose signal storage time period can be freely varied, there is, for instance, a frame interline transfer type charge-coupled device. The frame interline transfer type CCD 50, as represented in FIG. 6, is mainly constructed of a light reception section 52, a charge storage section 54, a horizontal CCD 55, a vertical CCD 56, an output stage 57 and a sweep-out drain 58.

A production of CCD output signals as represented in FIG. 7G will now be described with employing CCD 50 shown in FIG. 6.

Figure 6:
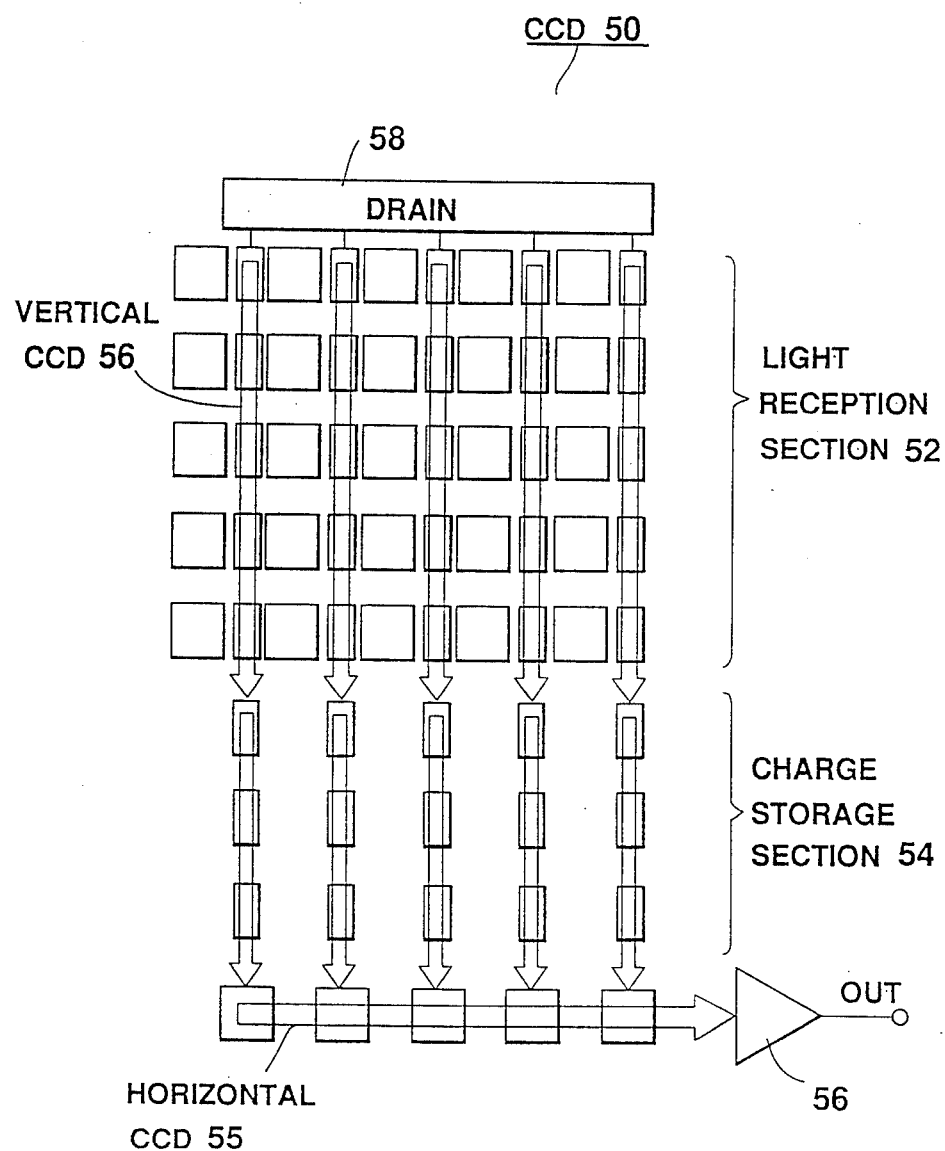
FIG. 6 schematically illustrates an internal circuit arrangement of a storage time period controlling type CCD employed in a color endoscope apparatus according to a third preferred embodiment; and, FIGS. 7A to 7G are timing charts of various signals in CCD shown in FIG. 6.

FIG. 7 is a timing chart for driving the frame interline transfer type CCD 50 shown in FIG. 6.

During vertical blanking period (see FIG. 7B), three different color light pulses R, G, and B (see FIG. 7A) are incident upon the light reception section 52 of CCD 50. These color light pulses R, G, and B are similarly produced from the above-described conventional light chopper having three RGB filters which are equi-distantly positioned and have wide widths, respectively.

An integration clear pulse (referred to as an "IC pulse" shown in FIG. 7C) is used to transfer the electron charges which have been stored in the pixels of CCD 50, to the vertical CCD 56. Then, the electron charges are ejected to the sweep-out drain 58 provided above the vertical CCD 56.

On the other hand, a field shift pulse (referred to as an "FS pulse" shown in FIG. FD) is also to transfer the electron charges which have been stored in the pixels of CCD 50, to the vertical CCD 56. These electron charges are further transferred to the charge storage section 54 positioned at the under position of CCD 50.

A signal time period for the color light pulse R is defined between the IC pulse "$A_1$" and FS pulse "$A_2$". That is, after the charge electrons which have been stored in the pixels of CCD 50 until an appearance of the IC pulse $A_1$, are transferred to the vertical CCD 56 at a time instant when the IC pulse "$A_1$" appears, they are swept-out to the sweep out drain 58. After the charge electrons which have been stored during the time period between appearances of the IC pulse "$A_1$" and FS pulse "$A_2$" have been transferred to the vertical CCD 56 at the time instant when the FS pulse $A_2$ appears, they are transferred to the charge storage section 54.

A signal time period for the light pulse "G" is determined by a time duration between appearances of the FS pulse "$A_2$" and "$B_2$"The charge electrons which have been stored into the pixels of CCD 50 since the appearance of the FS pulse "$A_2$", are transferred to the vertical CCD at the appearance of the FS pulse "$B_2$", and further transferred to the charge storage section 54. The charge electrons which have been stored into the pixels of CCD 50 since the appearance of the FS pulse "$B_2$" are transferred to the vertical CCD at the time instant of the appearance of the IC pulse "$B_1$", and thereafter are ejected by the sweep out drain 58.

A signal time period for the light pulse "B" is determined by a time duration between an appearance of the IC pulse "$B_1$" and an appearance of an FS pulse "$C_2$".

The signals which have been read from CCD 50 in accordance with the above-described operations, are produced as represented in FIG. 7G.

While repeatedly driving CCD 50 under the above explained RGB light pulse cycle, the CCD output signals having the desirable R, G, B time intervals are produced as illustrated in FIG. 7G.

While has been described above, in the frame sequentially scanning type color endoscope apparatus according to the invention, the time duration of at least one of three different color light pulses is set to be short as compared with those of the conventional color light pulses so that the blur phenomenon caused by the rapid movements of the object under examination can be avoided.

In particular, when the time interval between the red light pulse and green light pulse is selected to be shorter than that of the remaining blue light pulse, the resolution and color misregistration can be improved and moreover the signal-to-noise ratio of the resultant endoscope image can be increased.

In accordance with the present invention, the above-described basic idea of the invention may be applied to another type of color endoscope apparatus where the fiber scope is coupled to the TV camera.

What is claimed is:

1. A frame-sequential scanning type endoscope apparatus comprising:

light source means including; a lamp for sequentially producing a pulsatory light series in synchronism with a frame-sequential scanning operation of the endoscope apparatus; and a light chopper having a disk with first to third slots formed din its peripheral portion, red, green, and blue color filters mounted, respectively, on the corresponding first to third slots, the positions of said first and second slots being juxtaposed with each other with respect to the position of the third slot, said first to third slots each has the substantially same width, whereby red, green, and blue light pulses each having substantially same duration time are produced from the light chopper under the condition that a time interval between the red and green light pulses is shorter than at least another time interval between the red and blue light pulses;

light conducting means for sequentially receiving the red, green, and blue light pulses from the light source means at one end thereof and for successively projecting from the other end thereof the received three color light pulses onto an object under medical examination;

image sensing means positioned near the other end of the light conducting means, for sequentially receiving light pulses reflected from the illuminated object under medical examination so as to successively produce red, green, and blue image signals of the illuminated object; and image signal processing means for processing the red, green, and blue image signals derived from the image sensing means so as to obtain one complete color endoscope signal of the illuminated object.

2. A frame-sequential scanning type color endoscope apparatus as claimed n claim 1, wherein a frame scanning period with respect to each of said red, green, and blue image signals is selected to be approximately 11 milliseconds, wherein said duration time of each of the red, green, and blue pulses is selected to be approximately 3 milliseconds.

3. A frame-sequential scanning type color endoscope apparatus as claimed in claim 1, wherein said lamp is a xenon lamp.

4. A frame-sequential scanning type color endoscope apparatus as claimed in claim 1, wherein image sensing means includes:

a storage time controlling type charge-coupled device (CCD) for controlling the duration times of CCD output signals in response to the three different color light pulses.

5. A frame-sequential scanning type endoscope apparatus comprising:

a light source means including; a lamp for sequentially producing a pulsatory light series in synchronism with a frame-sequential scanning operation of the endoscope apparatus; and a light chopper having a disk with first to third slots formed in a peripheral portion of the disk, and red, green, and blue color filters, respectively, mounted on the corresponding first to third slots, the positions of said first and second slots being juxtaposed with each other with respect to a position of the third slot, each width of said first and second slots being narrower than the width of said third slots, whereby red and green light pulses each having a shorter duration time than a duration time of a blue light, the pulses being produced from the light chopper in such a manner that the time interval between the red and green light pulses is shorter than at least another time interval between the rd and blue light pulses;

light conducting means for sequentially receiving the red, green, and blue light pulses from the light source means at one end thereof and for successively projecting from the other end thereof the received three color light pulses onto an object under medical examination;

image sensing means positioned near the other end of the light conducting means, for sequentially receiving light pulses reflected from the illuminated object under medical examination so as to successively produce red, green, and blue image signals of the illuminated object; and, image signal processing means for processing the red, green, and blue image signals derived from the image sensing means so as to obtain one complete color endoscope signal of the illuminated object.

6. A frame-sequential scanning type color endoscope apparatus as claimed in claim 5, wherein the frame scanning period with respect to each of said red, green, and blue image signals is selected to be approximately 11 milliseconds, wherein said duration time of each of the red, green, and blue light pulses is selected to be approximately 3 milliseconds.

7. A frame-sequential scanning type color endoscope apparatus as claimed in claim 5, wherein said lamp is a xenon lamp.

8. A frame-sequential scanning type color endoscope apparatus as claimed in claim 5, wherein said image sensing means includes:

a storage time controlling type charge-coupled device (CCD) for controlling the duration times of CCD output signals in response to the three different color light pulses.

* * * * *